(12) United States Patent
Christrup et al.

(10) Patent No.: US 6,745,761 B2
(45) Date of Patent: Jun. 8, 2004

(54) INHALER

(75) Inventors: Søren Christrup, Struer (DK); Anders Geert-Jensen, Højbjerg (DK); Mikael Jørgensen, Århus C (DK); Jørgen Rasmussen, Struer (DK); Hugo Dines Schmidt, Århus C (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/464,757

(22) Filed: Jun. 19, 2003

(65) Prior Publication Data

US 2003/0230305 A1 Dec. 18, 2003

Related U.S. Application Data

(63) Continuation of application No. 10/096,174, filed on Mar. 13, 2002, now abandoned, which is a continuation of application No. 09/424,333, filed on Nov. 22, 1999, now abandoned.

(30) Foreign Application Priority Data

Sep. 24, 1998 (DK) .......................................... 1998 01207
Sep. 24, 1999 (SE) .................................. PCT/SE99/01683

(51) Int. Cl.7 ............................................... A61M 11/00
(52) U.S. Cl. ............................ 128/200.14; 128/200.22; 128/200.23
(58) Field of Search ........................ 128/200.14, 200.22, 128/200.23; 239/338

(56) References Cited

U.S. PATENT DOCUMENTS

| | | |
|---|---|---|
| 2,631,757 A | 3/1953 | Alexander |
| 2,965,100 A | 12/1960 | Bridges |
| 3,006,340 A | 10/1961 | Meshberg |
| 3,012,555 A | 12/1961 | Meshberg |
| 3,184,115 A | 5/1965 | Meshberg |
| 3,302,834 A | 2/1967 | Alsop |
| 3,456,644 A | 7/1969 | Thiel |
| 3,456,645 A | 7/1969 | Brock |
| 3,456,646 A | 7/1969 | Phillips et al. |
| 3,826,413 A | 7/1974 | Warren .................. 128/200.23 |
| 5,392,768 A | 2/1995 | Johansson et al. |
| 5,460,171 A | 10/1995 | Pesenti et al. |

*Primary Examiner*—Aaron J. Lewis
(74) *Attorney, Agent, or Firm*—Nixon & Vanderhye

(57) ABSTRACT

A breath actuated inhaler for delivering medicament by inhalation, comprising a housing having a mouthpiece and defining an air flow path extending from the mouthpiece through the housing; the housing holding a replaceable canister of medicament actuatable to deliver a dose of medicament into the air flow path, wherein the housing defines an opening in the air flow path and the opening is closed by a closure element connected to and replaceable with the canister. The closure element acts as a safety feature because it is only closed when the inhaler is used with a canister to which a closure element is connected the closure element carries an indication of the type of medicament in the canister to allow the user to recognise the type of medicament. A plurality of inhalers may be provided in which each given inhaler has an opening with a different shape and has a closure element with a shape which conforms with the opening of the given inhaler but which does not conform with the openings of the other inhalers.

22 Claims, 7 Drawing Sheets

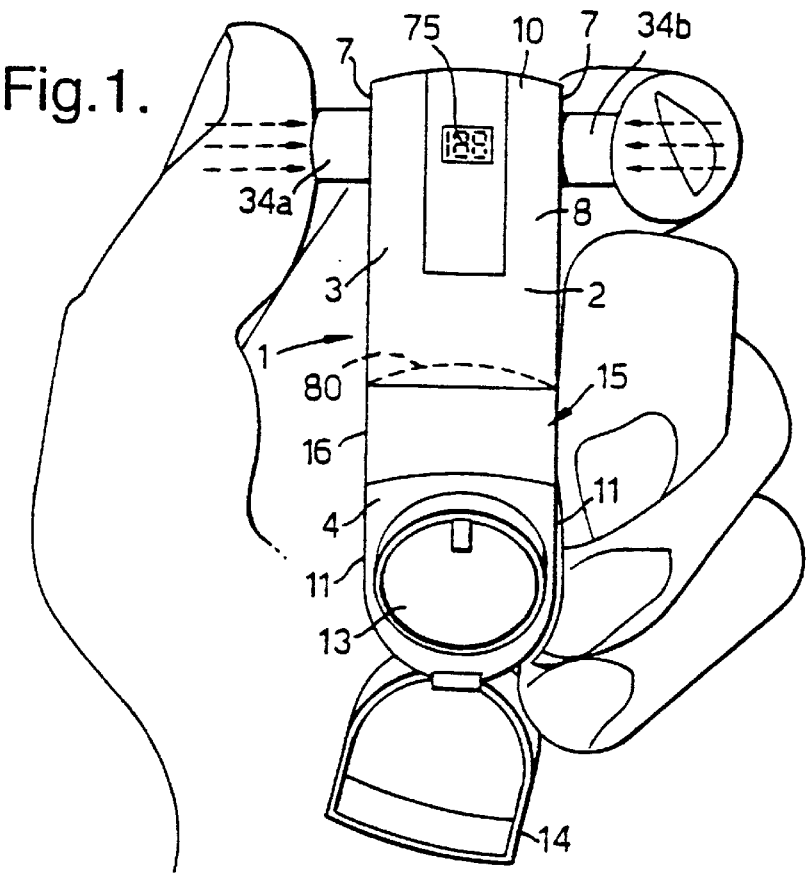
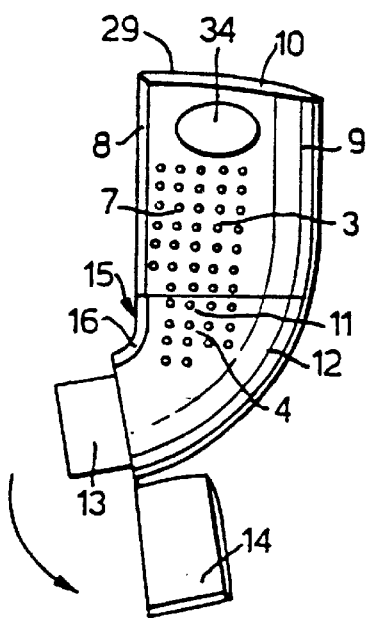
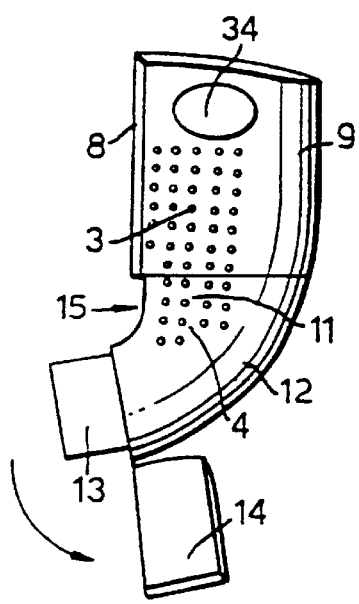

INHALER

This application is a continuation of application Ser. No. 10/096,174, filed Mar. 13, 2002 now abandoned, which is a continuation of application Ser. No. 09/424,333, filed Nov. 22, 1999, now abandoned, the entire content of which is hereby incorporated by reference in this application.

The present invention relates to an inhaler for delivery of medicament by inhalation, particularly but not exclusively to a breath-actuated inhaler.

BACKGROUND OF THE INVENTION

Inhalers are commonly used for delivery of a wide range of medicaments. The inhaler houses a canister of medicament which is actuated to deliver a dose of medicament through a mouthpiece. Desirably the canister is replaceable so that the inhaler is re-useable after the canister is empty or can be used with different medicaments. However, this advantage can create safety problems. In particular, it is difficult to control the type of medicaments supplied by inhalers. For example, users might insert a canister containing an inappropriate medicament as different medicaments are commonly supplied in similar canisters. Users might not know whether a given inhaler which comes to hand will deliver the desired medicament. Such problems are particularly serious when the inhaler is needed to provide a particular medicament urgently in an emergency. The present invention is intended to improve safety in an inhaler with a replaceable canister.

SUMMARY OF THE INVENTION

According to the present invention, there is provided an inhaler for delivering medicament by inhalation, comprising a housing having a mouthpiece and defining an air flow path extending from the mouthpiece through the housing; the housing holding a replaceable canister of medicament actuatable to deliver a dose of medicament into the air flow path, wherein the housing defines an opening in the air flow path and the opening is closed by a closure element connected to and replaceable with the canister.

The closure element acts as a safety feature because it is only closed when the inhaler is used with a canister to which a closure element is connected. This enables better control over the type of medicament to be delivered in that valid canisters can be provided with closure elements connected thereto. The absence of the closure element may be recognised by the user on insertion.

Advantageously, the closure element carries an indication of the type of medicament in the canister. In this way, the closure element may provide the advantage that it enables the type of medicament to be easily recognised by a user. It is particularly advantageous that the indication is provided on an element connected to the cannister itself so the risk of confusion is reduced.

The indication may be printed information, such as different colours, patterns, text or numbers or the colour of the closure element itself. Desirably, the indication is a tactile surface, for example an embossed or indented pattern. This enables a user with poor eyesight to recognise the type of medicament, which would not otherwise be possible, particularly in the case of an indication visible, say, through a window.

Preferably, the opening is defined in the outer surface of the housing. This enables the presence or absence of the closure element to be clearly visible to a user of the inhaler with the canister fitted.

Desirably, the opening is provided adjacent the mouthpiece. This allows for the closure element to be easily formed with a connection to the canister which itself is normally adjacent the mouthpiece to enable engagement in a nozzle block directing medicament out of the mouthpiece. Also it assists in making the indication visible because in normal use the inhaler will be held with the mouthpiece in view, facing the user.

The safety may be improved further if the present invention is applied to a breath-actuated inhaler further comprising an actuation mechanism arranged to be operated to actuate the canister by a flow through the air flow path, the opening being arranged, when open, to vent the flow sufficiently to prevent operation of the actuation mechanism. In this way, the inhaler will not provide medicament if inserted with a canister without a closure element, potentially containing inappropriate medicament, or if a canister is inserted in the incorrect position. This improves safety and gives the inhaler provider better control over the proper use of the inhaler.

The opening may be positioned and dimensioned to prevent operation at in the absence of a closure element at an inhalation level above the maximum expected flow rate at the mouthpiece. For example, operation may be prevented at a flow rate of at least eight times a standard inhalation flow rate. Conversely, it is unnecessary for the closure element when present to completely close the opening, provided that it closes the opening sufficiently to allow operation of the inhaler.

Typically in a breath-actuated inhaler wherein the actuation mechanism includes a trigger disposed in the air flow path responsive to the flow to cause operation of the actuation mechanism, for example by comprising a pre-loading mechanism arranged to store a loading force for actuation of the canister, the trigger being arranged to release the stored force.

The trigger is preferably a vane arranged to be physically moved by a flow through the air flow path, although an electronic trigger sensing the flow is a conceivable alternative.

The present invention is particularly suited to a common, simple form of breath actuated inhaler in which wherein the housing has outer walls defining a space which constitutes the air flow path.

Desirably, the opening is disposed in the air flow path between the trigger and the mouthpiece. This is an advantageous structure, because the inhalation flow generated by inhalation at the mouthpiece is drawn through the opening without thereby limiting the flow created within the air flow path at the trigger to prevent operation of the trigger.

Preferably the housing defines an inlet opening for the air flow path having a smaller opening area than the opening. This increases the air flow resistance at the opening relative to the opening which assists in ensuring the inhalation flow is vented by the opening in preference to the inlet opening, hence allowing the opening to prevent operation of the actuation mechanism.

According to a second aspect of the present invention, there are provided a plurality of inhalers according to the first aspect wherein each given inhaler has an opening with a different shape and has a closure element with a shape which conforms with the opening of the given inhaler but which does not conform with the openings of the other inhalers.

This provides the inhalers with a form of canister recognition. Inhalers are to be used exclusively with canisters having a closure element with a conforming opening. Use of canisters in inhalers which do not have a conforming opening may be recognised by the different shapes and may be prevented by the shapes of the opening and the closure element of a given inhaler prevent fitting of the closure element in an inhaler other than the given inhaler. Alternatively, the different shapes may the inhalers further comprise an actuation mechanism arranged to be operated to actuate the canister by a flow through the air flow path and the shape of the closure element of a given inhaler is such that when the closure element fitting in inhaler other than the given inhaler leaves open the opening of the other inhaler sufficiently open to prevent operation of the actuation mechanism of the other inhaler.

Accordingly the second aspect of the present invention makes it possible to control the use of canisters in particular inhalers. For example, the different shapes of opening and closure elements may be used for respective types of medicament to reduce the chances of cross-contamination between inhalers for differing medicaments.

With either aspect of the present invention, the canister and the closure element are connected by a connector which is arranged to prevent reconnection after separation of the canister and the closure element, for example by the connector is formed with a weak portion arranged to be broken in preference to the remainder of the connector on application of a force to separate the canister and the closure element. This further enhances the security of the present invention because it prevents a closure element from a valid canister being removed and attached to a new canister.

To allow a better understanding, an inhaler which embodies the present invention will now be described by way of non-limitative example with reference to the accompanying drawings, in which:

BRIEF DESCRIPTION OF THE DRAWINGS

FIG. 1 is a front view of the inhaler held in a hand;

FIG. 2 is a side view of the inhaler,

FIG. 2A is a side view of the inhaler without a closure element fitted;

DETAILED DESCRIPTION OF PREFERRED EMBODIMENTS

Figure 3:
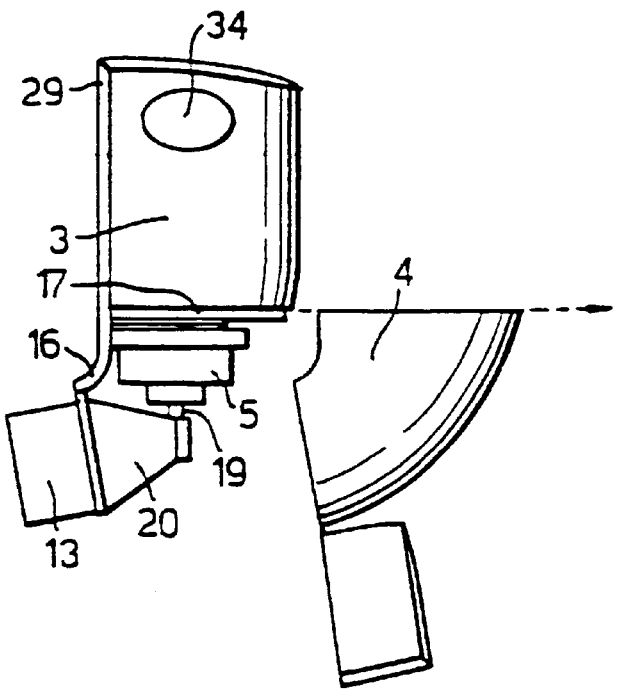
FIG. 3 is a side view of the inhaler with a lower housing portion being removed.

An inhaler 1 which embodies the present invention is illustrated in FIGS. 1 and 2, respectively showing the front view of the inhaler 1 held in a user's hand and a side view of the inhaler.

The inhaler has a housing 2 comprising an upper housing portion 3 and a lower housing portion 4 which are coupled together. The upper and lower housing portions 3 and 4 have outer walls which are hollow to define a space accommodating a canister 5 of medicament and an actuation mechanism 6 operatable to actuate the canister 5 to deliver a dose of medicament.

The upper housing portion 3 has opposed side walls 7 joined by a flat front wall 8, a curved rear wall 9 and a top wall 10. The lower housing portion 3 has opposed side walls 11 fitting flush with the side walls 7 of the upper housing portion 3 and a curved rear wall 12 fitting flush with the rear wall 9 of the upper housing portion 3. The rear walls 12 and 9 together form a curved surface comfortably received in the palm of the user's hand as illustrated in FIG. 1. A mouthpiece 13 protrudes from the lower housing portion 4 and may be protected by a cap 14 hinged to the lower housing member 4 to be openable as illustrated in FIG. 2.

The front of the lower housing member 4 between the side walls 11 is open to define an opening 15 in the outer surface of the housing 2 adjacent the mouthpiece 13 between the upper and lower housing portions 3 and 4. The opening 15 is closed by a closure element 16 fitting flush with the front wall 8 of the upper housing portion 3 to form part of the outer wall of the housing 2.

The upper and lower housing members are coupled by a coupling 17 allowing the lower housing member 4 to be slid off as illustrated in FIG. 3.

Figure 4:
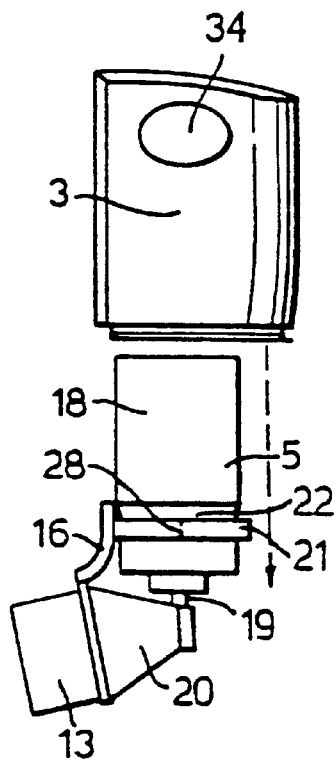
FIG. 4 is a side view of an upper housing portion of the inhaler with a canister being removed.

The canister 5 fits in the upper housing portion 3 and may be slidably removed for replacement as illustrated in FIG. 4.

The canister 5 comprises a generally cylindrical body 18 and a valve stem 19 which are compressible together to deliver a dose of medicament from the valve stem 19. The canister is of a known type including a metering chamber which captures a defined volume of medicament from the body 18 of the canister 5, which volume of medicament is delivered as a metered dose from the valve stem 19 on compression of the valve stem 19 relative to the body 18. The valve stem 19 is weakly biassed outwardly to reset the canister 5 after compression for refilling the metering chamber. The valve stem 19 is received in a nozzle block 20 which is arranged to direct a dose of medicament delivered from the valve stem 19 out of the inhaler 1 through the mouthpiece 13.

The closure element 16 is connected to the canister 5 by a collar 21 fitted around a necked portion 22 of the canister body 18. The collar 21 is permanently fixed to the closure element 16 and may be integral therewith. The collar 21 is restrained by the necked portion 22 of the canister 5 such that the closure element 16 is removed and replaced together with the canister 5 as illustrated in FIG. 4. The canister 5 and collar 21 have a small degree of relative movement along the axis of the canister 5. This allows actuation of the canister by compression of the canister body 18 towards the valve stem 19 when the stem 19 is fixed relative to the inhaler 1 in the nozzle block 20 and the collar 21 is also fixed by the closure element 16 fitting as part of the housing 2 of the inhaler 1.

Figure 5:
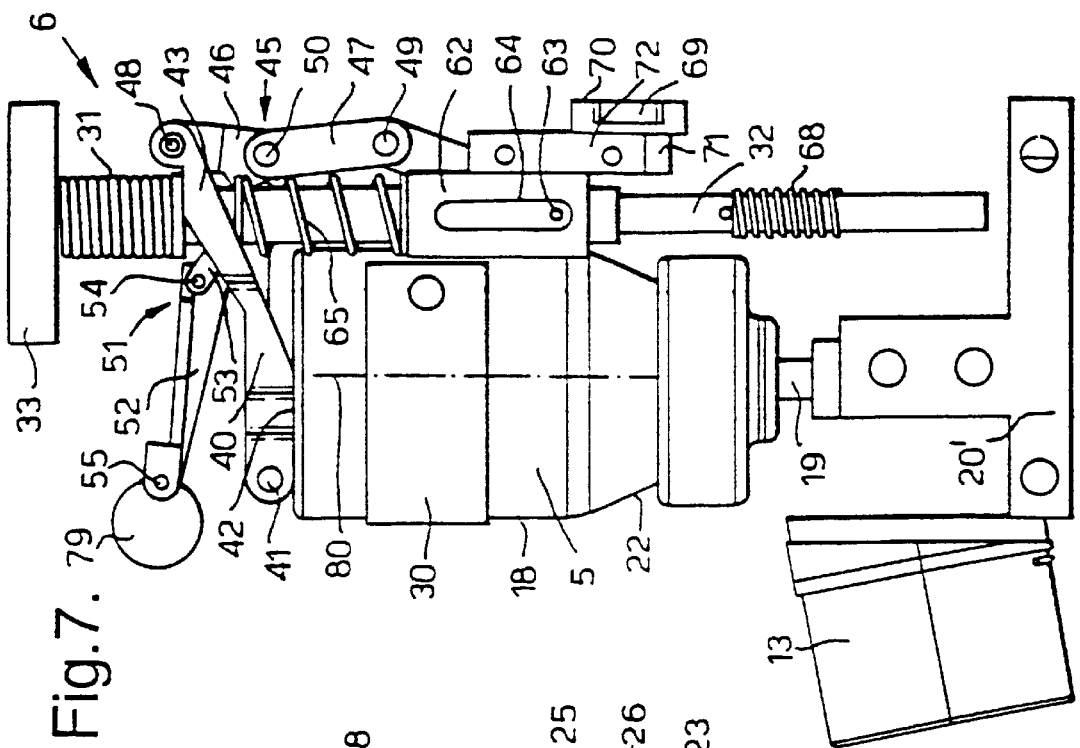
FIG. 5 is a side view of an alternative form of collar for connecting the closure element to the canister.
Figure 6:
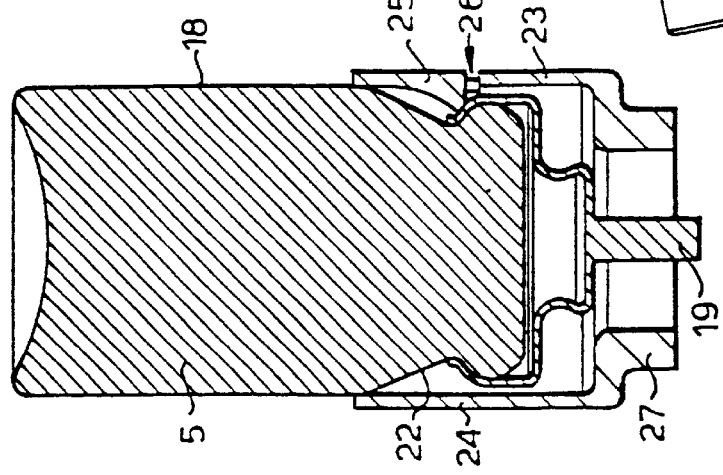
FIG. 6 is a cross-sectional view taken along line VI—VI in FIG. 5.

FIGS. 5 and 6 respectively illustrate a side view and cross-sectional view and alternative collar 23 for connecting the closure element 16 to the canister 5. The collar 23 includes a cylindrical portion 24 held on the necked portion 22 of the canister body 18 by a protrusion 25 formed in the cylindrical portion 24 by a U-shaped cut-out 26. The cylindrical portion 24 has an extension 27 extending beyond the end of the canister body 18 to protect the valve stem 19. The extension 27 is of reduced diameter relative to the remainder of the cylindrical portion 24 of the collar 23.

The force needed to separate either collar 21 or 23 from the canister preferably exceeds the normal strength of human fingers or hands, so in normal use the closure element is effectively permanently connected.

Optionally, the collars 21 and 23 are formed with a weak portion constituted by two rupture lines 28 disposed on opposite sides of the collar 21 or 23 and arranged to be broken preferentially to the remainder of the collar 21 or 23 on application of a force to separate the closure element 16 from the canister 5. After the rupture lines 28 have been broken or at least deformed to enable removal of the canister 5, it is impossible to connect the collar 21 or 23 to a different canister.

The outer surface of the closure element 16 carries an indication of the type of medicament in the canister 5 to which the closure element 16 is connected. The indication may be printed information, such as text, letters or numerals, or simply coloured patterns, an embossed or indented pattern or the colour of the closure element 16.

An inlet opening 29 is formed in the upper housing portion 3, in particular in its top wall 10 and front wall 8. The outer walls of the housing defined by the upper and lower portions 3 and 4 and the closure element 16 seal together to define a closed space which constitutes an air flow path extending from the mouthpiece 13 through the housing 2 to the inlet opening 29. Inhalation at the mouthpiece 13 creates a pressure differential which draws air in through the inlet opening 29 through that air flow path around the canister 5 and actuation mechanism 6 encased in the housing 2. The actuation mechanism 6 (described in detail below) has a trigger disposed in the upper housing portion 4 which, in response to a flow through the air flow path, triggers the actuation mechanism 6 to actuate the canister 5.

If a canister without a closure element connected thereto is inserted into the housing 2, then the opening 15 will remain open as illustrated in FIG. 2A. Consequently, when a user inhales at the mouthpiece 13, the flow resistance through the opening 15 will be much lower than the flow resistance through the remainder of the air flow path above the opening 15 from the inlet opening 29. Accordingly, the opening 15 will act as a vent most of the flow through the mouthpiece, thereby reducing the flow in the remainder of the air flow path in the upper housing portion through. The positioning of the opening 15 in the air flow path inside the housing 2 between the mouthpiece 13 and the trigger reduces the air flow across the trigger. The opening 15 is positioned and dimensioned such that the flow at the trigger is reduced below the threshold needed to operate the trigger and therefore prevents operation of the actuation mechanism 6. To assist in assuring that the opening 15 sufficiently vents the flow, the opening 15 is provided with a larger opening area and hence a lower flow resistance than the inlet opening 29. The opening 15 is dimensioned so that the actuation mechanism is not operated on a flow through the mouthpiece 13 at a level above the maximum expected inhalation, for example at an inhalation of at least eight times a standard inhalation flow rate. The triggering mechanism for the actuation mechanism 6 is designed taking into account the flow generated by a standard inhalation selected by the designer.

Figure 7:
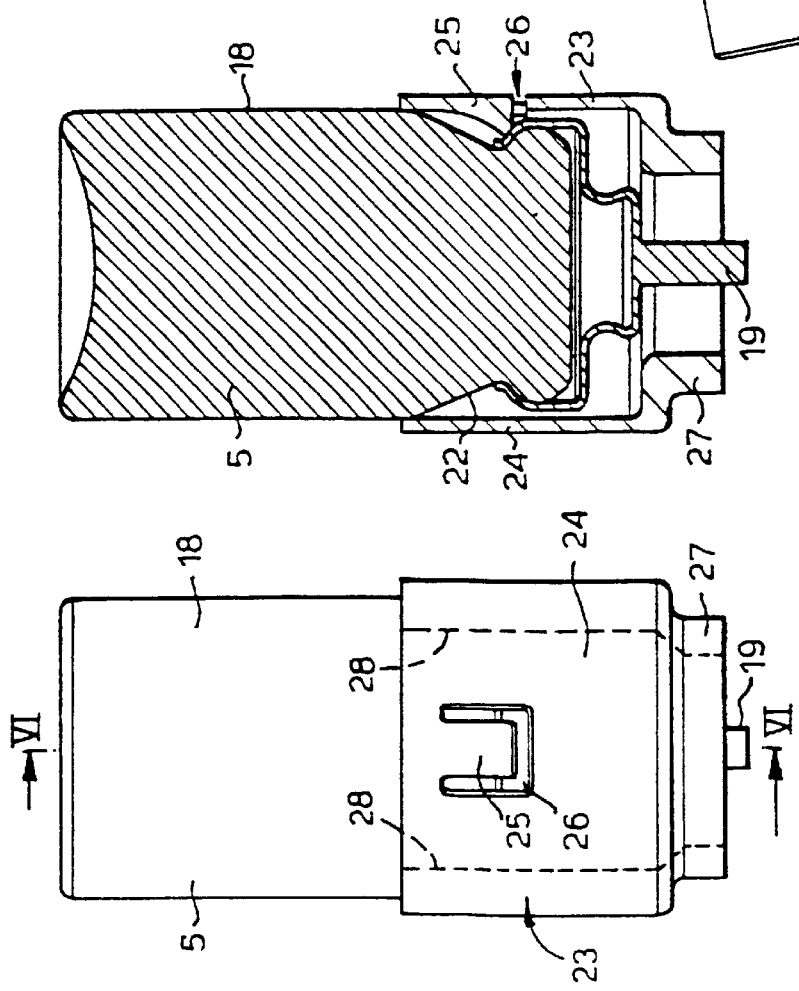
FIG. 7 is a side view of the canister mounting arrangement and actuation mechanism.
Figure 8:
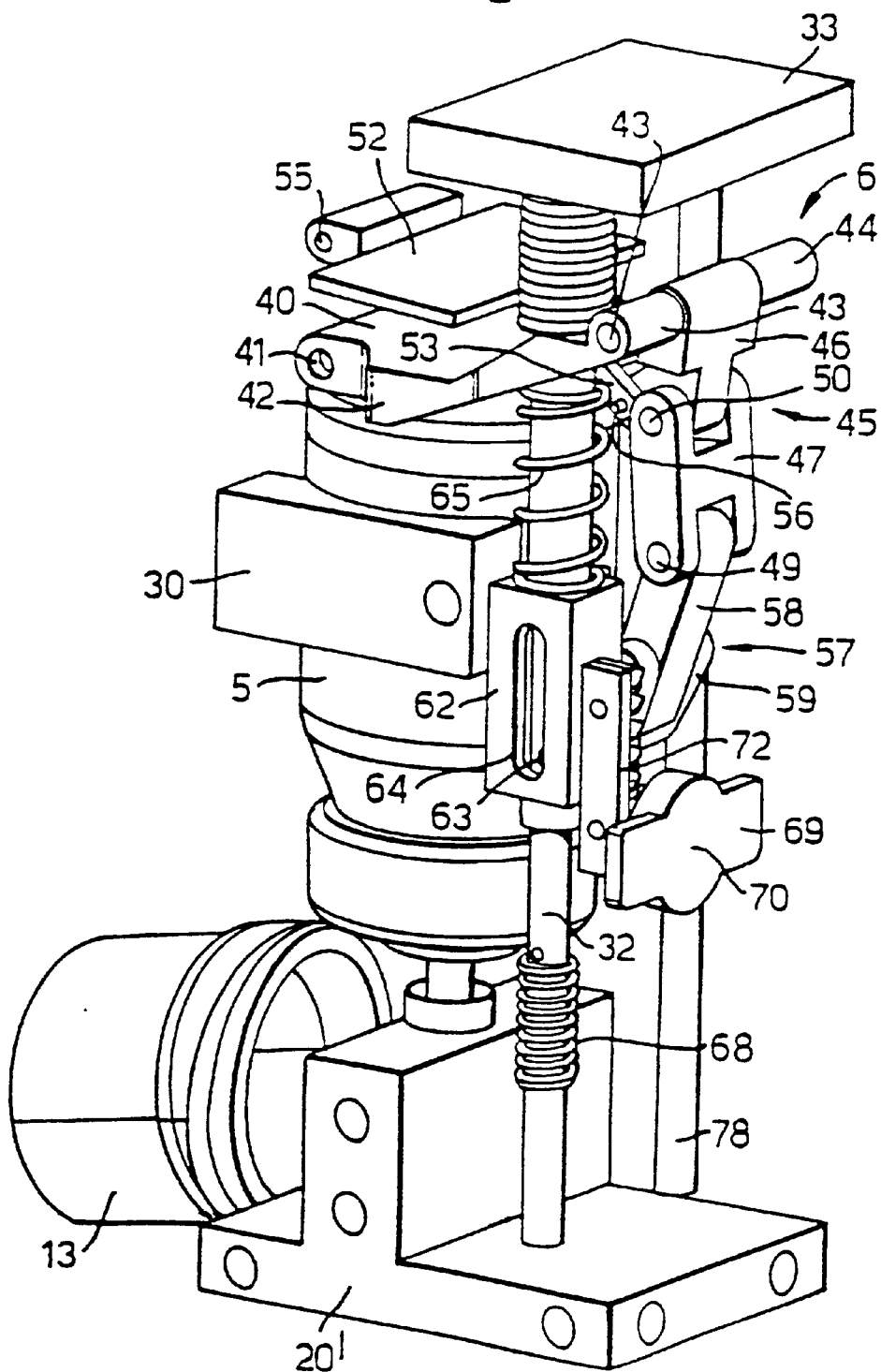
FIG. 8 is a view from the rear and side of the actuation mechanism.
Figure 9:
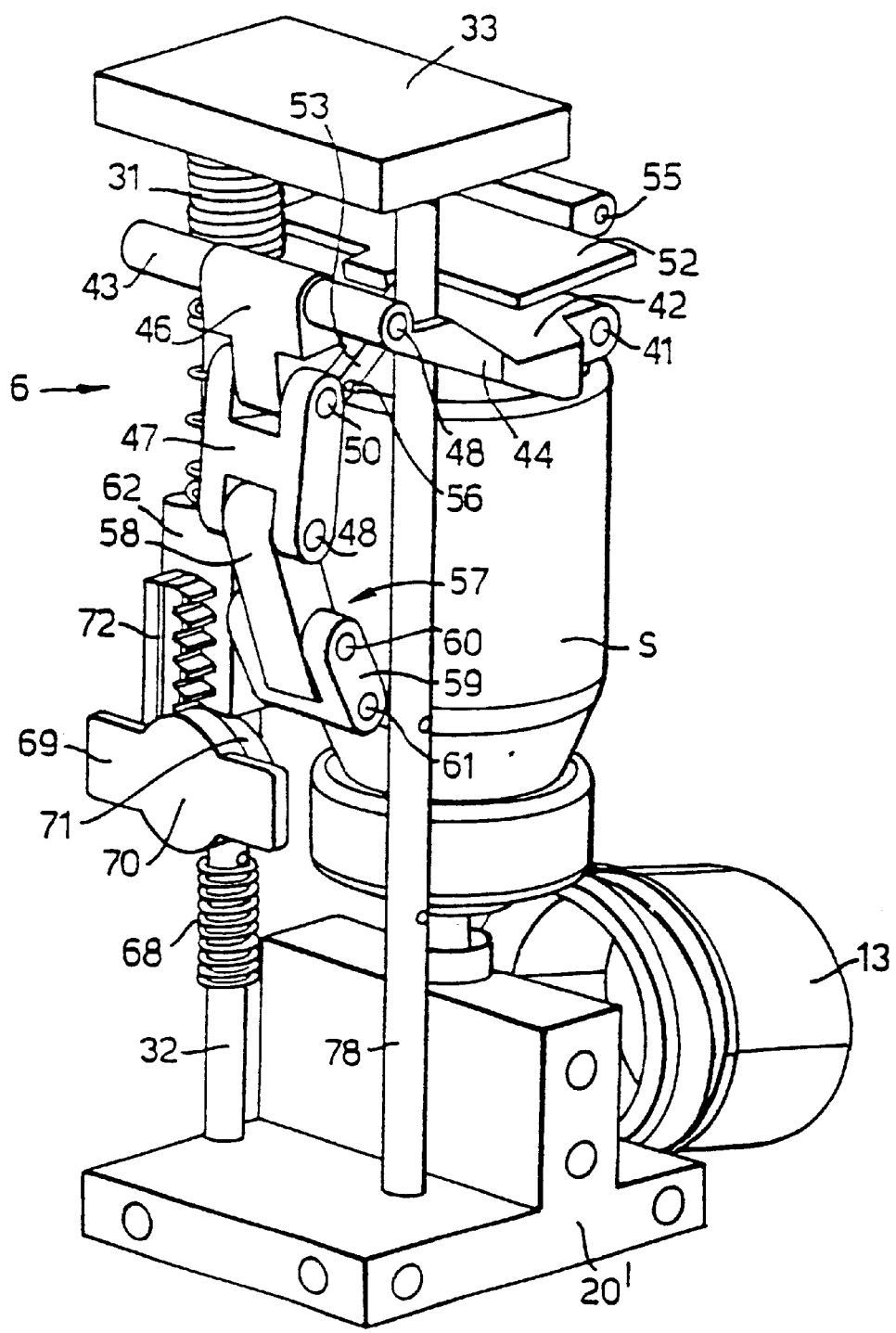
FIG. 9 is a view from the rear and the opposite side from FIG. 8 of the actuation mechanism.

The actuation mechanism 6 for actuating the canister 5 to deliver a dose of medicament is illustrated in FIGS. 7 to 9. The elements illustrated in FIGS. 7 to 9 are accommodated in the housing 2 but are illustrated separately for clarity. The canister 5 is held with its valve stem 19 in a nozzle block 20' connected to the mouthpiece 13, both fixed relative to the lower housing portion 4. A nozzle block 20' has a slightly different structural form from the nozzle block 20 illustrated in FIGS. 3 and 4 but performs the same function. The body 18 of the canister 5 is supported by a guide block 30 fixed to the upper housing portion 3 and having a curved inner surface engaging the cylindrical surface of the canister body 18 to allow axial movement of the canister body 18 within the housing 2. The actuation mechanism 6 operates to compress the canister body 18 relative to the valve stem 19 held in the nozzle block 20 to deliver a dose of medicament.

The structure of the actuation mechanism 6 is as follows.

The actuation mechanism 6 includes a pre-loading mechanism for loading a resilient loading element in the form of a coiled loading spring 31. The pre-loading mechanism includes the loading member constituted by a shaft 32 encircled by the coils of the loading spring 31. The shaft extends and is movable in a direction parallel to the cylindrical axis 80 of the canister body 18. The loading member shaft 32 has an enlarged head 33.

Figure 10:
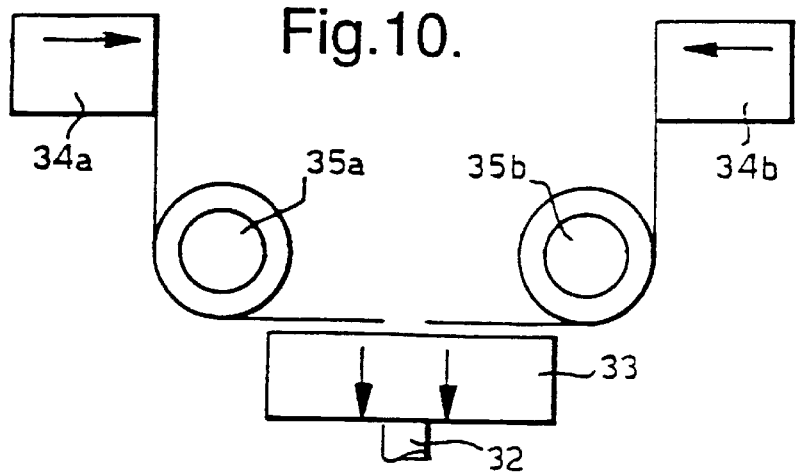
FIG. 10 is a front view of the arrangement for loading the actuation mechanism.

As illustrated in FIG. 1, two buttons 34a and 34b, constituting contact members to be manually depressed, are mounted opposite one another in the side walls 7 of the upper housing portion 3 on either side of the axis 80 of the canister 5 held in the housing 2. The buttons 34 are manually depressible in a direction substantially perpendicular to the axis 80 of the cannister 5 which makes them easy to grip and move by a finger and thumb, as can be seen in FIG. 1. The buttons 34 load the loading member 32 and loading spring 31 through the arrangement illustrated in FIG. 10 comprising two torsion springs 35a and 35b fixed inside the upper housing portion. The torsion springs 35a and 35b engage the enlarged head 33 of the loading member 32 and respective ones of the buttons 34 to convert sideways force applied to the buttons 34 to a downwards force along the axis of the loading member shaft 32.

Figure 11:
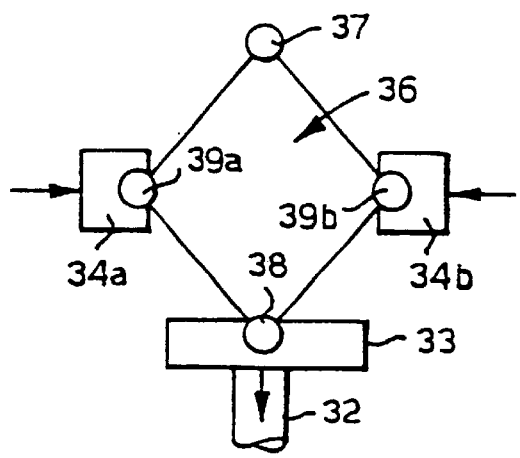
FIG. 11 is a side view of an alternative form of button arrangement for loading the actuation mechanism.

An alternative means for converting the sideways force applied to the buttons 34 is illustrated in FIG. 11. This consists of a double knee joint 36 fixed at its upper end 37 to the upper housing portion 3, fixed at its lower end 38 to the enlarged head 33 of the loading member 32 and fixed at its intermediate joints 39a and 39b to the respective buttons 34a and 34b.

The pre-loading mechanism further includes a lever 40 pivoted relative to the housing about a pivot 41. The lever 40 has a planar canister engagement portion 42 contacting the canister body 18 adjacent the pivot 41 with a pair of arms 43 and 44 extending therefrom. One arm 43 is engaged by the loading spring 31 so that the loading spring 31, when loaded, biasses compression of the canister through the lever 40 coupled to the canister 5 by the canister engagement portion 42. As the loading spring 31 is further away from the pivot 41 than the cannister engagement portion 42, this provides leverage between the loaded actuation force and the force applied to the cannister 5. The arm 43 has a hole through which the loading member shaft 32 extends. The other arm 44 of the lever 43 has a similar hole through which extends a further shaft 78 for preventing lateral displacement of the lever 40.

The actuation mechanism further includes a triggering mechanism for holding the lever 40 against compression of the canister under the biassing of the spring 31 and to release the lever 40 in response to inhalation at the mouthpiece. The triggering mechanism is constructed as follows.

The triggering mechanism comprises a first knee joint 45 having two links 46 and 47 connected pivotally to one another by a central pivot 50. The upper link 46 is pivotally connected both arms 43 and 44 of the lever 40 by a pivot 48. The lower link 47 is pivotally connected to the upper housing portion 3 by a pivot 49.

Accordingly, the first knee joint 45 has a locked position illustrated in FIGS. 7 to 9 in which it holds the lever 40 against compression of the canister 5. In the locked position of the first knee joint 45, the central pivot 50 is substantially aligned with the pivots 48 and 49 at the ends of the links 46 and 47. As the first knee joint 45 is connected to the lever at a position further away from the pivot 41 then the cannister engagement portion 42, this provides leverage between the locking force provided by the first knee joint and the force applied to the cannister 5. This leverage enhances the locking and triggering action of the triggering mechanism.

The triggering mechanism further includes a second knee joint 51 comprising two links 52 and 53 connected by a central pivot 54. One link 57 of the second knee joint 51 is pivotally connected to the upper housing portion 3 by a pivot 55 and extends laterally so that it constitutes a trigger vane which is moved by a flow of air thereover. The trigger vane 52 has a counterweight portion 79 (illustrated only in FIG. 7) fixed to the opposite side of pivot 55 from the laterally extending surface. The counterweight balances the trigger vane so that its centre of mass is positioned on the axis of the pivot 55.

The other link 53 of the second knee joint 51 extends from the trigger vane 52 between the arms 43, 44 of the lever 40 to the upper link 46 of the first knee joint 45 where it is pivotally connected by a pivot 56.

Accordingly, the second knee joint 51 has a locked position illustrated in FIGS. 7 to 9. In the locked position of the second knee joint, the central pivot 54 is substantially aligned with the pivots 55 and 56 and the ends of the links 52 and 53.

The actuation mechanism 6 further includes a reset mechanism which is constructed as follows.

The reset mechanism employs a locking element constituted by a third knee joint 57 comprising an upper link 58 and a lower link 59 pivotally connected together by a central pivot 60. The upper link 58 is pivotally connected to the upper housing portion 3 by the pivot 49 in common with the first knee joint 45. The lower link 59 is pivotally connected to the loading member shaft 32 by a pivot 61. The third knee joint 57 has a locked position illustrated in FIGS. 7 to 9 in which it holds the loading member shaft 32 in its loaded position as illustrated in FIG. 7. In the locked position of the third knee joint 57, the central pivot 60 is aligned with the pivots 48 and 61 at the end of the links 53 and 59. The third knee joint 57 is also biassed into its locked position by a biassing spring 67 connected to the upper housing portion 3. Hence the third knee joint constitutes a locking element which holds the canister in a compressed state through spring 31 and lever 40 after the full movement of the lever 40 to compress the canister 5.

The reset mechanism further includes a release member 62 mounted on the loading member shaft 32 by having an aperture through which the shaft 32 extends. The release member 62 is movable relative to the shaft 32 between limits defined by a pin 63 protruding from the shaft 32 engaging in a track 64 formed in the release member 62. A timer spring 65, the coils of which encircle the shaft 32, is connected between the arm 43 of the lever 40 and the release member 62. The timer spring 65 is in a relaxed state in FIG. 7 and is provided for biassing the release member 62 when loaded by movement of the lever 40 to compress the canister 5.

Figure 12:
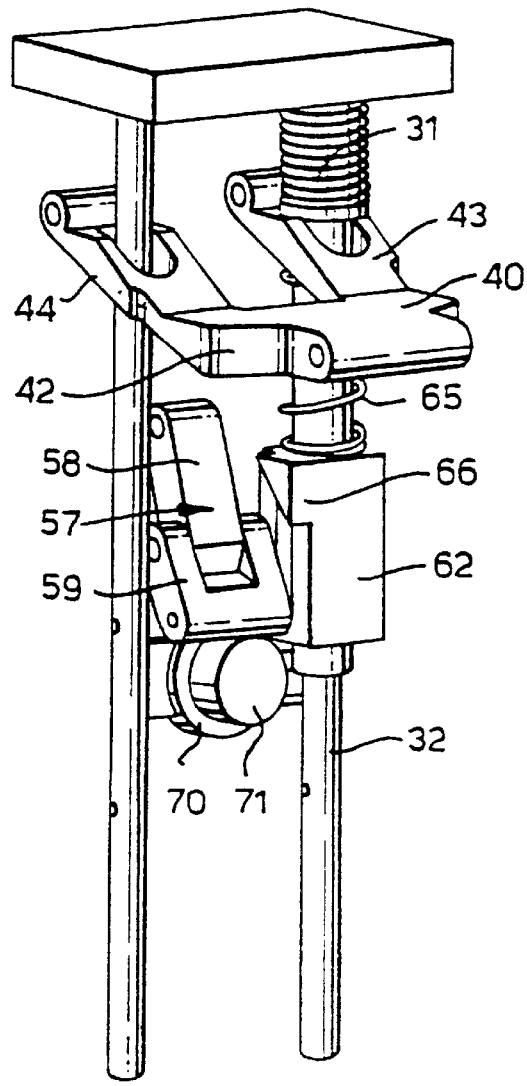
FIG. 12 is a view of certain parts of the actuation mechanism from the front and side.

A protrusion 66 extends from the release member 62 (as best seen in the partial view of FIG. 12) to engage with the lower link 59 of the third knee joint 57 when the release member 62 is moved down the shaft 32. Such engagement of the protrusion 56 with the third knee joint 57 moves the knee joint 57 against the biassing spring 67 to break the third knee joint 57 thereby releasing locking effect of the third knee joint 57.

The shaft 32 is biassed upwardly by a reset spring 68 acting between the shaft 32 and upper housing portion 3 to move the shaft 32 upwardly upon breaking of the third knee joint 57.

The downwards movement of the release member 62 is damped by a damping element 69 consisting of a stator 70 fixed to the upper housing portion 3 and a rotor 71 rotatable through viscous fluid provided between the rotor 71 and stator 70. The rotor 71 is driven by a toothed rack 72 connected to the release member 62.

Operation of the actuation mechanism 6 will now be described with reference to FIGS. 13 to 16 which illustrate the various parts of the actuation mechanism 6 in schematic form for ease of understanding.

Figure 13:
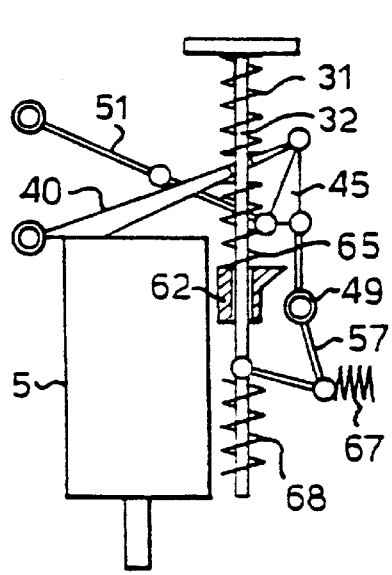
FIGS. 13 to 16 are schematic views of the actuation mechanism illustrating respective states over a complete cycle of operation.

FIG. 13 illustrates the neutral state in which the loading member shaft 32 is in its uppermost position, so that the loading spring 31 is relaxed. In this state, the first and second knee joints 45 and 51 are both in their locked positions. The timer spring 65 and the reset spring 68 are relaxed.

Figure 14:
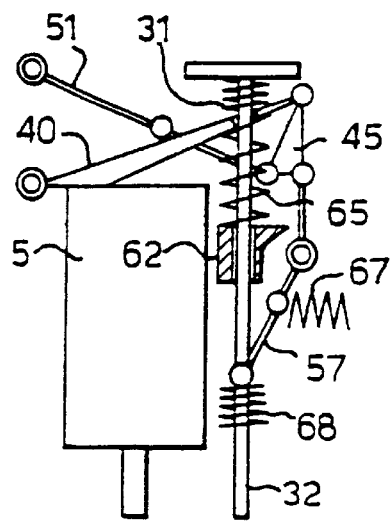
Figure 15:
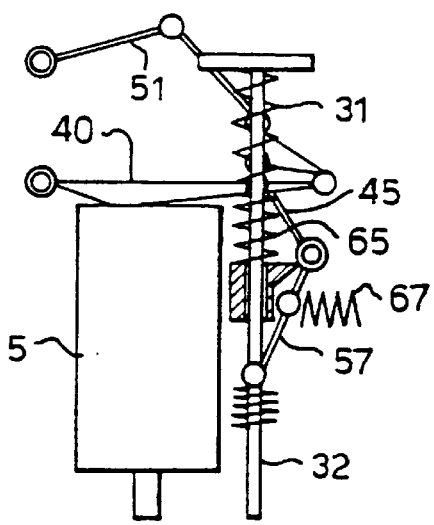

Upon depression of the buttons 34, the loading member shaft 32 is moved downwardly to a second position illustrated in FIG. 14 loading the loading spring 31 which therefore biasses the lever 40 towards compression of the canister 5. However, the first knee joint 45 is its locked position where it holds the lever 40 against compression of the canister 5. The first knee joint 45 is held in its own locked position by the second knee joint 51 being in its locked position.

Movement of the loading member shaft 32 downwards also loads the reset spring 68 and brings the third knee joint 57 into its locked position where it is held by the spring 67. In this loaded state illustrated in FIG. 14, the inhaler 1 is loaded ready for delivery of a dose of medicament.

Inhalation by the user at the mouthpiece 13 generates an air flow through the air flow path defined inside the housing 2 from the inward opening 29 to the mouthpiece 13. This air flow acts on the trigger vane 55 of the second knee joint 51 causing it to move upwardly due to pressure drop created by the flow inside the housing 2 to the position illustrated in FIG. 15 where the second knee joint is broken. This breaks the first knee joint 45 into its broken position illustrated in FIG. 15 which releases the lever 40 and allows it to compress the canister 5 under the biassing of the loading spring 31.

During compression of the canisters, the shaft 32 remains locked in position by the third knee joint 57. This causes the canister to be held in its compressed state by the shaft 32 acting through the spring 31 and lever 40, the spring force of the spring 31 far exceeding the internal reset biassing of the canister 5.

Figure 16:
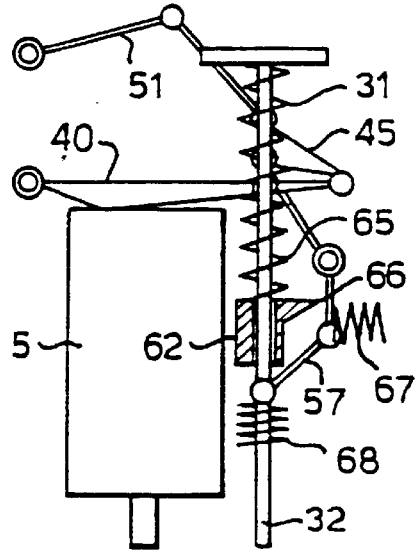
Figure 17:
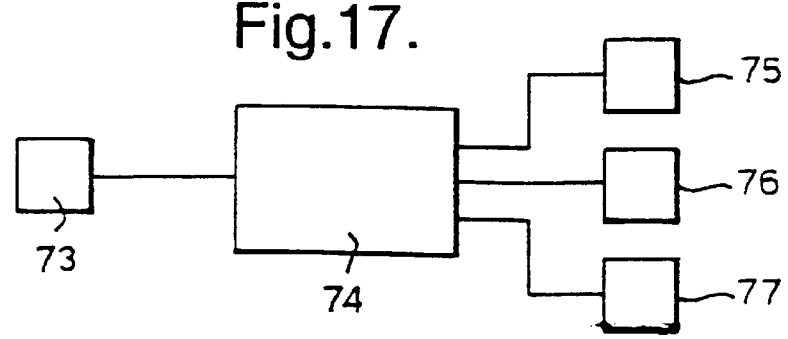
FIG. 17 is a view of the electronic timer circuit.

However, movement of the lever 40 loads the timer spring 65 which accordingly biasses the release member 62 downwards. Movement of the release member 62 is delayed by the damping action of the damping element 69. The protrusion 66 of the release element 62 engages the third knee joint 57 after a predetermined period of time after actuation of the canister 5. This time is determined by the strength of the timer spring 65 and the damping properties of the damping element 69 and is at least 100 ms or 200 ms and up to 1000 ms or 5000 ms to allow the full dose of medicament to be delivered from the cannister 5. Such engagement breaks the third knee joint 57 into its broken position as illustrated in FIG. 16. Subsequently the reset spring 68 moves the loading member shaft 32 upwardly to the neutral position illustrated in FIG. 13. At the same time the shaft 32 lifts the release member 62, itself still damped by the damping element 69 so that the reset movement is damped.

Release of the shaft 32 causes the spring 31 to raise the lever 40 which has two effects. Firstly it allows the canister to reset itself. Secondly, it causes the first and second knee joints 45 and 51 to straighten, returning them to their locked position in the neutral position of the actuator mechanism illustrated in FIG. 13. The loading spring 31 and the timer spring 65 are pre-loaded and do not work against the reset movement, so that the reset spring 68 has only to overcome friction and the weight of the component.

The buttons 34a and 34b protrude from the inhaler when the actuation is in its relaxed state as shown in FIG. 1 and are depressed to a position flush with the side walls 8 of the upper housing portion 3. Accordingly, the distance between the extremities of the buttons before depression is less than the maximum length of the inhaler 1 in the direction parallel to the axis 80 of the canister 5 and less than the overall length of the canister 5 including the body 18 and the valve stem 19. Also, the total distance over which the two buttons 34 are moved relative to one another is greater than the distance by which the body 18 and the valve stem 19 of the canister 5 are relatively compressed. This is achieved by the leverage obtained by the loading spring 31 engaging lever 40 at a point further away from the pivot 41 than the canister engagement portion 42.

The actual flow recommended in order to correctly deliver a drug will depend on the manner operation of the drug, the position where it should be deposited in the mouth, lungs of the user and the manner of dispensing the drug. Some drugs are inhaled as a fine mist and transported all the way to the lungs whereas others are inhaled like a jet of liquid deposited in the mouth of the person. These different types of drugs require different types of inhalation and therefore different inhalation flows and different actions by the user.

It is possible to adapt each of a number of different inhalers for use with a number of different types of drug by giving each inhaler an opening with a different shape and giving different closure elements shapes which conform with a single type of inhaler. For example, a possible different shape is illustrated by the dotted line in FIG. 1. Thus canister with differently shaped closure elements are for use exclusively with the inhaler having a conforming opening. The different shapes may prevent a closure element from being fitted in an inhaler of the inhaler having a conforming opening. Alternatively, the closure element may fail to close the vent of an inhaler having a differently shaped opening such that the remaining opening vents the flow sufficiently to prevent operation of the triggering mechanism.

What is claimed is:

1. An inhaler for delivering medicament by inhalation, comprising:

a housing having a mouthpiece and defining an air flow path extending from the mouthpiece through the housing;

the housing holding a replaceable canister of medicament actuatable to deliver a dose of medicament into the air flow path, said housing defining an opening in the air flow path, said opening being closed by a closure element connected to and replaceable with the canister;

an actuation mechanism for actuating the canister by a flow through the air path, said opening, when open, venting the flow sufficiently to prevent operation of the actuation mechanism, said actuation mechanism comprising a trigger in the form of a vane disposed in the air flow path and moveable physically by a flow through said air flow path.

2. An inhaler according to claim 1, wherein the closure element carries an indication of the type of medicament in the canister.

3. An inhaler according to claim 2, wherein the indication is a tactile surface.

4. An inhaler according to claim 1, wherein the opening is defined in the outer surface of the housing.

5. An inhaler according to claim 4, wherein the opening is provided adjacent the mouthpiece.

6. An inhaler according to claim 1, wherein the housing has two coupled portions which are separable to allow insertion of a canister and which are shaped to define the opening between the two portions when coupled together.

7. An inhaler according to claim 1, wherein the housing has outer walls defining a space which constitutes the air flow path.

8. An inhaler according to claim 1, wherein the actuation mechanism further comprises a pre-loading mechanism arranged to store a loading force for actuation of the canister, the trigger being arranged to release the stored force.

9. An inhaler according to claim 1, wherein the opening is disposed in the air flow path between the trigger and the mouthpiece.

10. An inhaler according to claim 1, wherein the housing defines an inlet opening for the air flow path having a smaller opening area than the opening.

11. An inhaler according to claim 1, wherein the canister and the closure element are connected by a connector which is arranged to prevent reconnection after separation of the canister and the closure element.

12. An inhaler according to claim 11, wherein the connector is formed with a weak portion arranged to be broken in preference to the remainder of the connector on application of a force to separate the canister and the closure element.

13. An inhaler according to claim 1, wherein the closure element is connected to a collar fitted around a necked portion of the canister as a connector between the canister and the closure element.

14. A plurality of inhalers each according to claim 1, wherein each given inhaler has a opening with a different shape and has a closure element with a shape which conforms with the opening of the given inhaler but which does not conform with the opening of the other inhalers.

15. A plurality of inhalers according to claim 14, wherein the shapes of the opening and the closure element of a given inhaler prevent fitting of the closure element in an inhaler other than the given inhaler.

16. A plurality of inhalers according to claim 14, wherein the inhalers further comprise an actuation mechanism arranged to be operated to actuate the canister by a flow through the air flow path and the shape of the closure element of a given inhaler is such that when the closure element fitting in inhaler other than the given inhaler leaves open the opening of the other inhaler sufficiently open to prevent operation of the actuation mechanism of the other inhaler.

17. A plurality of inhalers each according to claim 1, wherein the canisters held in different inhalers store different types of medicaments and the closure elements of the different inhalers carry respective different indications of the types of medicament in the canisters to which they are connected.

18. An inhaler for delivery of a medicament by inhalation, comprising a housing having a mouthpiece and defining an air flow path extending from the mouthpiece through the housing, the housing being arranged to hold a replaceable canister of medicament actuatable to deliver a dose of medicament into the air flow path, wherein the housing defines an opening in the air flow path arranged to be closed by a closure element connected to the canister.

19. A canister adapted for use in an inhaler according to claim 18 having connected thereto a closure element for closing the opening in the air flow path defined in the housing of the inhaler.

20. A canister inhaler according to claim 19, wherein the canister and the closure element are connected by a connector which is arranged to prevent reconnection after separation of the canister and the closure element.

21. A canister according to claim 20, wherein the connector is formed with a weak portion arranged to be broken in preference to the remainder of the connector on application of a force to separate the canister and the closure element.

22. A canister according to claim 18, wherein the closure element is connected to a collar fitted around a necked portion of the canister as a connector between the canister and the closure element.

* * * * *